United States Patent [19]

Slavicek

[11] Patent Number: 5,853,982
[45] Date of Patent: Dec. 29, 1998

[54] **METHOD OF ISOLATING STRAINS OF THE *LYMANTRIA DISPAR* NUCLEAR POLYHEDROSIS VIRUS**

[75] Inventor: James M. Slavicek, Dublin, Ohio

[73] Assignee: The United States of America as represented by the Secretary of Agriculture, Washington, D.C.

[21] Appl. No.: 943,785

[22] Filed: Oct. 3, 1997

[51] Int. Cl.$^6$ .............................. C12Q 1/70; C12N 7/00; C12N 7/02
[52] U.S. Cl. ........................... 435/5; 435/235.1; 435/239
[58] Field of Search ........................... 435/5, 6, 7.1, 7.2, 435/7.21, 235.1, 239

[56] References Cited

U.S. PATENT DOCUMENTS

| | | | |
|---|---|---|---|
| 3,876,772 | 4/1975 | Bierl et al. | 424/84 |
| 4,911,913 | 3/1990 | Hostetter et al. | 424/93.6 |
| 4,945,057 | 7/1990 | Temeyer et al. | 530/388.4 |
| 5,132,220 | 7/1992 | Shapiro et al. | 435/235.1 |
| 5,180,581 | 1/1993 | Miller et al. | 424/93.2 |
| 5,244,805 | 9/1993 | Miller | 435/320.1 |
| 5,266,317 | 11/1993 | Tomalski et al. | 424/93.2 |
| 5,352,451 | 10/1994 | Miller et al. | 424/93.2 |
| 5,420,031 | 5/1995 | Slavicek et al. | 435/235.1 |
| 5,462,732 | 10/1995 | Slavicek et al. | 424/93.2 |

FOREIGN PATENT DOCUMENTS

WO 90/10387  9/1990  WIPO.

OTHER PUBLICATIONS

Burand, John P., et al., "Alternation of *Autographa californica* Nuclear Polyhedrosis Virus DNA upon Serial Passage in Cell Culture," *Virology*, 119:223–229 (1982).

Cusack, T., et al., Effect of Serial Passage on Genetic Homogeneity of a Plaque Variant of *Lymantria dispar* Nuclear Polyhedrosis Virus (Hamden LDP–67), *J. Gen. Virol.*, 70:2963–2972 (1989).

Fraser, M.J., et al., "Acquisition of Host Cell DNA Sequences by Baculoviruses: Relationship Between Host DNA Insertions and FP Mutants of *Autographa californica* and *Galleria mellonella* Nuclear Polyhedrosis Viruses," *Journal of Virology*, 47(2):287–300 (Aug. 1983).

Lynn, Dwight E., "Enhanced Infectivity of Occluded Virions of the Gypsy Moth Nuclear Polyhedrosis Virus for Cell Cultures," *Journal of Invertebrate Pathology*, 63:268–274 (1994).

Podgwaite, John D., et al., "Effects of Aerially Applied Gypchek on Gypsy Moth (Lepidotera: Lymantriidae) Populations in Maryland Woodlots," *Journal of Economic Entomology*, 85 (4):1136–1139 (Aug. 1992).

Slavicek, James M., "Analysis of Viral Genomic Heterogeneity in the *Lymantria Dispar* Nuclear Polyhedrosis Virus Formulation Gypchek," *International Symposium on Applications of Biotechnology to Tree Culture, Protection and Utilization*, Columbus, Ohio, Aug. 5–8, 1991.

Slavicek, James M., "Enhancement of *Lymantrai Dispar* Nuclear Polyhedrosis Virus Efficacy, Potency, and Polyhedra Production in Cell Culture Through Biotechnology," *Proceedings of the Annual Gypsy Moth Conference*, Nov. 4–7, 1991.

Slavicek, James M., et al., "Properties of Two *Lymantria dispar* Nuclear Polyhedrosis Virus Isolates Obtained from the Microbial Pesticide Gypchek," *Journal of Invertebrate Pathology*, 59:142–148 (1992).

*Primary Examiner*—David Guzo
*Attorney, Agent, or Firm*—Janet I. Stockhausen; M. Howard Silverstein; John D. Fado

[57] ABSTRACT

A method of isolating a gypsy moth virus that maintains normal levels of viral occlusion when produced in an insect cell line is disclosed. This method comprises the steps of cycles of infecting gypsy moth larvae with a strain of gypsy moth virus of interest, harvesting the larvae to collect budded virus, infecting a cell line capable of propagation in a bioreactor and then harvesting the virus. One repeats the infection cycle until one has enriched for a gypsy moth virus strain with normal levels of occlusion.

12 Claims, 2 Drawing Sheets

FIG. 2

METHOD OF ISOLATING STRAINS OF THE *LYMANTRIA DISPAR* NUCLEAR POLYHEDROSIS VIRUS

BACKGROUND OF THE INVENTION

Chemical pesticides and fungicides are the most commonly used control agents for forest insect pests and fungal diseases. In excess of 350 billion pounds of these agents are used annually in the United States to control pests and diseases in forestry, agriculture, and residential areas. Broad spectrum insecticides and fungicides have adverse impacts not only on their target organisms but also on beneficial insects and fungi, and consequently, on the entire ecosystem. In addition, chemical residues may cause health problems among the human population.

Interest in biological insect control agents is growing as a consequence of concerns regarding chemical pesticide use. Insect baculoviruses are one group of insect biological control agents that have received considerable attention. These viruses have been isolated from hundreds of insect species, exhibit relatively narrow host ranges, can be aerially applied to agricultural crops and forests, and can be manipulated through genetic engineering to enhance viral efficacy (Tinsley and Harrap, *Comp. Virol.* 12:1–101, 1978; Bonning and Hammock, *Biotechnol. Genet. Eng. Rev.* 10:455–489, 1992; and Miller, *J. Invertebr. Pathol.* 65:211–216, 1995 for reviews). Insect baculoviruses have essentially no adverse environmental impact due to their specificity for their target host. Long-term environmental hazards and health concerns are not a factor with biological control agents because chemical residues are not present. Unfortunately, biological control agents exhibit several disadvantages in comparison to chemical controls, including cost of production, efficacy, and stability.

One particularly troublesome tree pest is the gypsy moth. The gypsy moth was imported from France in 1869 and used to produce fibers for silk at Bedford, Massachusetts, a suburb of Boston. Since its release or escape from containment the gypsy moth has spread throughout most of New England, New York, Pennsylvania, Maryland, New Jersey, Virginia, West Virginia, Ohio, and Michigan, and is also present in North Carolina and Wisconsin (McFadden, et al., *Forest Insect Guilds: Patterns of Interactions with Host Trees*, Y. N. Baranchikov, et al., pp. 172–186, U.S. Department of Agriculture, For. Serv. Gen. Tech. Rep. NE-153, Radnor, Pa., 1989; Blackburn, et al., *Proceedings of the Annual Gypsy Moth Review*, pp. 261–351, 1994). Several chemical pesticides, including DDT, have been successfully used for gypsy moth control.

Knowledge of the adverse environmental impacts of DDT and other chemical insecticides has caused a shift to less harmful chemicals such as diflubenzeron, and to the biorational agent, *Bacillus thuringiensis* (Bt) for gypsy moth control. The *Lymantria dispar* nuclear polyhedrosis virus (LdMNPV), is also used, on a limited basis, as a gypsy moth control agent. The LDMNPV has the significant advantage over other gypsy moth control agents of specificity for the gypsy moth. Consequently, LdMNPV is the agent of choice for gypsy moth control in environmentally sensitive areas and areas that contain threatened and endangered insects. However, LDMNPV is not used extensively due to lack of commercial scale production. Currently, LdMNPV is produced on a limited basis by the Forest Service and the Animal and Plant Health Inspection Service in gypsy moth larvae. Production in larvae is expensive, and currently costs approximately $15.00 to generate sufficient virus to treat an acre of forest. In contrast, diflubenzeron and Bt cost approximately $3.00 and $4.00, respectively, for enough product to treat one acre of forest.

Production of LDMNPV in cell culture, or in vitro, systems is an alternative to production in larvae and has the advantages of a controllable production system, a pure product, and a lower cost. An insect cell line (a fat body cell line) that produces high numbers of LdMNPV polyhedra has been developed (Lynn, et al., *Appl. Environ. Microbiol.* 55:1049–1051, 1989). However, this cell line was not useful in bioreactors due to high shear sensitivities. Other gypsy moth cell lines, e.g., the Ld652Y cell line, are able to be propagated in bioreactors. The Ld652Y cell line exhibits good growth characteristics in bioreactors. This cell line exhibits a doubling time of approximately 20 hours, and can withstand sparging shear-stress. Furthermore, the Ld652Y cell line is the only gypsy moth cell line that has been shown to exhibit the attributes necessary for successful propagation in bioreactors to date. However, polyhedra produced in the Ld652Y cell line by wild-type virus contain significantly fewer viral particles compared to polyhedra produced in gypsy moth larvae. Consequently, the potency of polyhedra produced in the Ld652Y cell line is significantly less compared to the potency of polyhedra produced in gypsy moth larvae.

What is needed in the art of the gypsy moth control is an improved strain of LdMNPV that retains the ability to occlude wild-type amounts of viral nucleocapsids when produced in an insect cell line capable of propagation in a bioreactor.

BRIEF SUMMARY OF THE INVENTION

The present invention is a method of isolating a gypsy moth virus that maintains normal levels of virion occlusion when produced in an insect cell line, preferably Ld652Y.

In a preferred form of the present invention, the method comprises first infecting gypsy moth larvae per os with the strain of gypsy moth virus of interest and then harvesting the larvae to collect budded virus within the insect hemolymph. An insect cell line capable of propagation in a bioreactor, preferably Ld652Y, is then infected with the budded virus preparation, and the virus is harvested after propagation in the cell line. One then repeats the in vivo/in vitro infection cycle, preferably at least three times, until one has enriched for a gypsy moth virus strain with normal levels of occlusion. One will preferably assay the resultant viral strain for number of occluded particles.

During the infection cycles the viral strains are adjusted to an infection dose that would give a percentage of mortality (preferably 10–25%) that ensures that some of the insects are infected with one virus particle. This infection dose adjustment enriches the population for strains with normal occlusion potential.

The present invention is also the viral strain that is produced from the method described above.

The present invention is also a method of isolating a gypsy moth virus that exhibits adequate potency when produced in an insect cell line, such as the Ld652Y cell line. This method additionally comprises the step of analyzing the resultant viral strain for potency. Typically, viral potency is defined as the number of polyhedra necessary for a sufficient degree (at least 80–90%) of insect mortality.

The present invention is also a method of protecting plants from the gypsy moth, comprising applying to a leaf surface or insect habitat an insecticidally effective amount of a gypsy moth virus having the identifying characteristics described above.

The present invention is also an insecticidal composition comprising an insecticidal amount of a gypsy moth virus having the characteristics described above.

It is an object of the present invention to control insect pests.

It is another object of the present invention to provide an LDMNPV that maintains normal levels of virion occlusion when produced in the Ld652Y cell line or other insect cell lines capable of propagation in a bioreactor.

It is an advantage of the present invention that insect control may be provided at lower cost.

Other objects, advantages and features of the present invention will become apparent after review of the specification, drawings and claims.

BRIEF DESCRIPTION OF THE SEVERAL VIEWS OF THE DRAWINGS

FIG. 2 is a graphical representation of the distribution of virion densities in polyhedra cross-sections in polyhedra generated by LDMNPV isolate A21-MPV-12 produced in gypsy moth larvae and the Ld652Y cell line.

DETAILED DESCRIPTION OF THE INVENTION

1. Brief Overview

Figure 1:
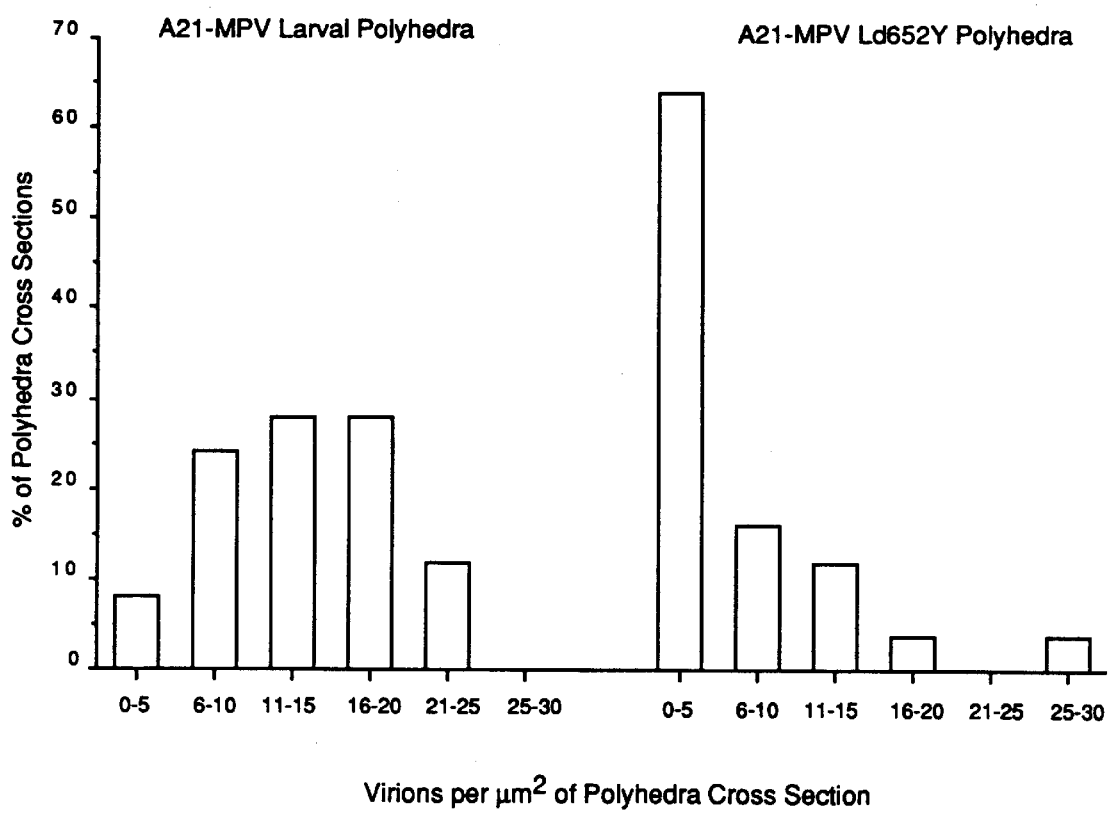
FIG. 1 is a graphical representation of the distribution of virion densities in polyhedra cross-sections in polyhedra generated by LDMNPV isolate A21-MPV produced in gypsy moth larvae and the Ld652Y cell line.

The general field of the present invention is methods of controlling tree pests, such as the gypsy moth (*Lymantria dispar*). Specifically, the field of the present invention is a method of isolating strains of the *Lymantria dispar* nuclear polyhedrosis virus (LdMNPV) that maintain normal virion occlusion when produced in the Ld652Y cell line.

Nuclear polyhedrosis viruses have two distinct morphological forms (Blissard and Rohrmann, *Annu. Rev. Entomol.* 35:127–155, 1990). The infection cycle begins with ingestion of a polyhedron, a polyhedral-shaped crystalline protein matrix that contains virus particles. The polyhedron is dissolved within the insect midgut, thereby releasing the occluded virus particles that then infect the insect. Early after infection a budded form of virus is produced from an infected cell and gives rise to a systemic infection within the insect larval host. Late in infection virions are produced that become occluded into polyhedra, which is the form of the virus used for insect control.

We have developed a method of isolating LdMNPV strains that maintain normal levels of virion occlusion when produced in the Ld652Y cell line. By "normal" or "wild-type" levels of virion occlusion, we mean that the level of virion occlusion in insect cell lines, such as the Ld652Y cell line, is at least 90% that of the same virus in gypsy moth larvae.

In contrast, polyhedra produced in the Ld652Y cell line by wild-type virus exhibits a significant drop in the amount of viral particles occluded into polyhedra. Furthermore, wild-type virus produced in the Ld652Y cell line also exhibit a significant drop in potency compared to virus produced in gypsy moth larvae. The drop in potency of polyhedra produced in the Ld652Y cell line is due to the drop in virion occlusion. The occlusion of normal amounts of viral particles results in potencies equal to or greater than the potency of GYPCHEK. GYPCHEK is the form of LDMNPV being produced in gypsy moth larvae by the USDA for use in gypsy moth control programs. The production of polyhedra in the Ld652Y cell line that have a potency at least as high as GYPCHEK is necessary in order for production in this cell line to be economical.

2. Production of a strain of LdMNPV with normal levels of occlusion in Ld652Y cell line In one embodiment, the present invention is a method of isolating a gypsy moth virus strain that maintains normal or wild-type levels of virion occlusion when produced in an insect cell line such as Ld652Y.

One first selects an LDMPV strain of interest. The method described herein is thought to be successful for any strain of LdMPV.

One then infects gypsy moth larvae per os, preferably as described below in the Examples. Preferably, the amount of virus used for these infections should result in approximately 5–40% mortality, most preferably 10–25% mortality, because at a low mortality level it is likely that larvae are infected with one or just a few viral particles. After infection, preferably 10 days after, the larvae are bled to obtain budded virus present in the insect hemolymph. The hemolymph is purified, preferably as described below, and a viral inoculum obtained from the hemolymph is used to infect insect cells capable of propagation in a bioreactor. For the Examples below, Ld652Y cells were used. Ld652Y cells are typically infected with hemolymph inoculum at 0.1 $TCID_{50}$ units/cell.

After infection, polyhedra are isolated. The polyhedra are then again used to infect gypsy moth larvae, as described above, and once again larvae are bled to obtain budded virus which are used to infect an insect cell line. Preferably, the in vivo/in vitro selection protocol is repeated three times before the viral titer is adjusted. In the Examples below, at the third in vivo infection, larvae mortality is as high as 96%. At this point, the viral dose is decreased, preferably to approximately $1\times10^4$ polyhedra/ml for the fourth through sixth in vivo infections.

After the last in vivo infection, the budded virus is plaque-purified and analyzed. The Examples below describe preferable methods of analyzing the virus strain for occlusion. In the most preferable form of the present invention, the new viral strain will exhibit virion occlusion levels of at least 90%, preferably at least 94%, that of the same strain produced in *L. dispar* larvae. Most preferably, polyhedra produced by the strain in Ld652Y cells contain an equal or greater number of virions compared to polyhedra produced in *L. dispar* larvae.

One preferably repeats the in vivo/in vitro cycle until a significant increase in potency is measured (at least doubling of mortality). In the Examples below, three cycles were needed. Preferably, one then continues the cycles to achieve purification.

The present invention is also a method of producing a viral strain with wild-type potency. The Examples below describe viral strains with an $LC_{90}$ measurement at least equal to, and preferably greater than, that of GYPCHEK produced in larvae. A suitable strain of the present invention will have a potency at least 90% that of GYPCHEK.

The present invention is also viral strain produced by the method described above. Preferably, viral strain has the characteristics of normal occlusion and high potency in Ld652Y cells.

EXAMPLES

1. Analysis of polyhedra produced by wild-type LdMNPV isolates.

Polyhedra produced in gypsy moth larvae and the Ld562Y cell line were analyzed by electron microscopy to determine the relative amount of viral nucleocapsids present within polyhedra. Polyhedra were fixed in sodium cacodylate buffer, pH 6.2 (0.05M sodium cacodylate, 0.5 mM HCL), containing 1% glutaraldehyde at 4° C. for 20 minutes. Polyhedra were then fixed in sodium cacodylate buffer with 3% glutaraldehyde for 1 hour at 4° C. The samples were washed 3× in sodium cacodylate buffer over a 1 hour period. The samples were postfixed in sodium cacodylate buffer containing 2% osmium tetroxide for 2.5 hours at ambient temperature, and then washed 3× in sodium cacodylate buffer over a 1 hour period. Molten agar was added to the samples (final concentration 2%) and allowed to gel; the samples were cut into 1 mm$^2$ blocks and incubated overnight in 35% ethanol. The samples were dehydrated through incubation in an ethanol series (35, 50, and 70% with 2% uranylacetate, 85, 95, and 100%-3X) for 5–7 minutes at each step, except for the 70% step which was for 1 hour. The samples were then washed 3X (10 minutes each wash) in propylene oxide. The polyhedra were infiltrated over a 24 hour period with propylene oxide:Poly/Bed.812 (25.55 g poly bed, 13.5 g dodecenylsuccinic anhydride, 10.9 g nadic methylanhydride, Polysciences) at 2:1, 1:1, and 1:2 ratios. After infiltration the polyethylene capsules were flushed with freon and filled with Poly/Bed 812 containing 2% DMP 30 (Polysciences), incubated at 35° C. for approximately 15 hours, 45° C. for 8 hours and finally at 60° C. overnight. The samples were sectioned with a diamond knife on a Reichert-Jung Ultracut E43 microtome, the sections stained for 20 minutes in 5% uranylacetate in methanol, poststained in lead nitrate (2.7% lead citrate, 3.5% sodium citrate, 0.16 N NaOH), and viewed with a transmission electron microscope. Polyhedra cross-sections were photographed, and the number of virions present within cross-sections were quantified by counting. The polyhedra were sectioned randomly with respect to the cutting plane, thereby generating representative cross-sections of polyhedra. Statistical analysis of data was performed using the StatView program from Abacus Concepts (Berkeley, Calif.).

Polyhedra generated by the wild-type isolates A21-15, A21-MPV, B21-A, and 163-B in the Ld652Y cell line were found to contain significantly fewer viral nucleocapsids compared to polyhedra generated by the same isolates in gypsy moth larvae (Table 1). The observed 25 decrease in virion occlusion was significant (ANOVA, Fisher's PLSD, P<0.05). The decrease in virion occlusion ranged from approximately 42% to 55%.

TABLE 1

Comparison of virion densities within polyhedra produced in gypsy moth larvae and in the Ld652Y cell line by unselected LdMNPV strains.

| | Virions/$\mu m^2$ | | |
|---|---|---|---|
| Viral Isolate | Polyhedra Produced In *L. dispar* larvae | Polyhedra Produced in Ld652Y cells | Percent Decrease |
| A21-15 | 15.3 | 7.1 | −53.6 |
| A21-MPV | 13.6 | 6.1 | −55.1 |
| B21-A | 14.9 | 8.6 | −42.3 |
| 163-B | 16.9 | 7.9 | −55.1 |

The distribution in ranges of virion densities within polyhedra generated in gypsy moth larvae and the Ld652Y cell line were compared. The relative virion densities in polyhedra were graphed in the form of the percentage of polyhedra cross-sections containing from 0–5, 6–10, 11–15, 16–20, 21–25, and 25–30 virions per $\mu m^2$ of polyhedra cross-section surface area. The distribution of virion densities of isolate A21-MPV polyhedra gave a bell-shaped curve (FIG. 1). The majority of cross-sections contained from 11–15 and 16–20 virions per $\mu m^2$. In contrast, distribution of virion densities of isolate A21-MPV produced in the Ld652Y cell line was asymmetrical. The majority of polyhedra cross-sections contained from 0–5 virions per $\mu m^2$ of cross-section surface area (FIG. 1). However, a few polyhedra were found to contain a high number of viral particles. This finding suggested that a viral variant may be present within the population that had either retained the ability to occlude wild-type amounts of viral particles or had mutated to a viral form that was capable of occluding a large number of viral particles when polyhedra are generated in the Ld652Y cell line.

2. Analysis of wild-type virus potency.

The potency of virus produced in gypsy moth larvae and the Ld652Y cell line were compared. The *L. dispar* 652Y (Ld652Y) ovarian cell (Goodwin, et al., *In Vitro* 14:485–494, 1978) was propagated in complete medium (Goodwin's IPL-52B medium, JRH Biosciences, Lexena, KS; with 10% heat-inactivated fetal bovine serum, Hyclone, Logan, UT, and 6.25 mM glutamine, Gibco, BRL).

Flasks (Corning, T-150) were seeded with $5\times10^6$ Ld652Y cells and infected with 0.1 $TCID_{50}$ units of the plaque-purified virus isolates. Seven days post-infection (p.i.) the polyhedra were harvested by centrifugation at 550 g for 5 minutes. The polyhedra pellet was resuspended in 5 ml of the complete medium and sonicated for 30 seconds. The polyhedra were pelleted by centrifugation at 550 g and resuspended in phosphate buffered saline (PBS; 0.14 M NaCl, 2.7 mM Kcl, 10 mM $Na_2HPO_4$, 1.8 mM $KH_2PO_4$).

Polyhedra produced in the Ld562Y cell line were used to generate in vivo polyhedra. Fourth instar gypsy moth larvae were infected per os by placing them on a diet containing surface-applied polyhedra ($2.5\times10^5$ per $mm^2$ of diet surface). Larvae were collected as they died, and polyhedra were isolated from homogenized larvae by centrifugation at 550 g. The polyhedra were resuspended in PBS and then recentrifuged as described above. This process was repeated 3 or 4 times.

Bioassays were performed as described in Slavicek, et al. (*J. Invertebr. Pathol.* 59:142–148, 1992). Briefly, polyhedra were suspended in 10 ml of sterile 0.05 M Tris-HCL buffer, pH 6.2, and briefly sonicated to disperse the polyhedra. A 100 mg lyophilized sample of standard gypsy moth virus, Gypchek, was similarly suspended and vigorously ground in a glass tissue homogenizer for 3 minutes. Five serial 10-fold dilutions of each of the stock virus suspensions were prepared in Tris buffer. Dilutions were prepared such that final polyhedra concentrations in diet fed to test insects ranged between $1\times10^2$ and $1\times10^7$/ml. One milliliter of dilution was added to 99 ml of tempered (52° C.) diet and vigorously mixed with a variable-speed stirrer (5000 rpm) for 30 seconds. Virus-treated diet was cooled and cut into 1.25 $cm^3$ cubes.

Each virus dosage was presented to five groups of 10 newly molted second instar larvae from a standard laboratory strain of the gypsy moth (New Jersey). Each group of 10 larvae was confined to a 100×15 mm plastic petri dish and given two 1.25 $cm^3$ virus-treated diet cubes on which to feed for 48 hours. Larvae were reared in a growth chamber at 24°±2° C. under a 16/8 hour light/dark photoperiod and observed daily for mortality. Dead larvae were removed and examined microscopically to confirm virus deaths. Mortality data were examined by Probit analysis using a POLO-PC program (LeOra Software, Berkeley, Calif.).

The potencies of polyhedra produced in gypsy moth larvae and in the Ld652Y cell line by LDMNPV isolates A21-15, A21-MPV, B21-A, and 163-B were determined and compared. The potency of polyhedra produced in larvae with all four isolates was significantly greater than the potency of polyhedra produced in the Ld652Y cell line (Table 2). The decrease in potency ranged from approximately 22-fold to 130-fold. The decrease in virion occlusion provides a basis for the drop in the potency of polyhedra produced in the Ld652Y cell line compared to polyhedra generated in larvae. The use of polyhedra produced in the Ld652Y cell line would require application of approximately 20 to 40-fold more polyhedra than if virus is produced in larvae for effective control. Consequently, the cost of the use of polyhedra generated in the Ld652Y cell line would be prohibitive unless a means of generating LDM-NPV strains that occluded wild-type levels of viral particles were developed.

TABLE 2

Comparison of the potencies of wild-type viral isolate polyhedra produced in gypsy moth larvae and the Ld652Y cell line.

| Viral Isolate | $LC_{90}$ Larval Polyhedra[a] | $LC_{90}$ Ld652Y Polyhedra[a] | $LC_{90}$ Ld652Y/ $LC_{90}$ Larval |
|---|---|---|---|
| A21-15 | 16,200 | 733,045 | 45.2 |
| A21-MPV | 3,696 | 482,816 | 130.6 |
| B21-A | 834,904 | 18,444,380 | 22.1 |
| 163-B | 29,207 | 624,128 | 21.4 |

[a]Polyhedra/ml of diet.

3. Isolation of viral strains that occlude wild-type amounts of viral particles in polyhedra produced in the Ld652Y cell line.

We devised a selection protocol to generate a strain of LdMNPV that retained normal occlusion characteristics in polyhedra produced in the Ld652Y cell line. Polyhedra from several LdMNPV plaque-purified isolates were used to infect gypsy moth larvae per os. Fourth instar gypsy moth larvae were placed on diet containing $5 \times 10^4$ polyhedra/ml and allowed to feed ad libitum for a period of 48 hours. The amount of virus used for these infections resulted in approximately 10–40% mortality. At low mortality levels it is likely that larvae were infected with one or just a few viral particles. Ten days after infection, the larvae were bled to obtain budded virus present in the hemolymph. The hemolymph was spun in an Eppendorf table top centrifuge at 14,000 rpm for 10 minutes to remove large debris. 100 $\mu$l of hemolymph was added to 9.90 ml of complete medium, and passed through a series of syringe filters (5, 1.2, and 0.45 $\mu$m) for further purification. The medium/hemolymph was then used as inoculum to infect $2 \times 10^6$ Ld652Y cells at approximately 0.1 $TCID_{50}$ units per cell. Seven days after infection the polyhedra were isolated as described earlier. The polyhedra were then used to infect fourth instar gypsy moth larvae as described above, and larvae were bled to obtain budded virus which was used to infect Ld562Y cells as described above. By infecting gypsy moth larvae at a low dose with polyhedra produced in the Ld562Y cell line, the polyhedra that are most infectious have the greatest probability of infecting the larvae. Consequently, the strain of virus that produces polyhedra with high amounts of viral particles, and hence the most infectious polyhedra, will be selected for. The in vivo/in vitro selection protocol described above was repeated 3 times. At the third in vivo infection larval mortality was as high as 96%. Consequently, the viral dose was decreased to $1 \times 10^4$ polyhedra/ml for the fourth through the sixth in vivo infections. After the sixth in vivo infection, budded virus was plaque-purified. Several viral lines taken through the in vivo/in vitro selection process (termed selected isolates) were chosen for further analysis.

4. Analysis of selected LDMNPV isolates.

The relative amounts of virion occlusion in polyhedra produced in gypsy moth larvae and the Ld652Y cell line by the selected virus strains were determined and compared. Polyhedra produced in gypsy moth larvae and the Ld652Y cell line by the selected isolates exhibited similar levels of virion occlusion (Table 3). There was no significant difference in relative virion occlusion in polyhedra produced in the Ld652Y cell line compared to polyhedra generated in gypsy moth larvae (NOVA, Fisher's PLSD). This result indicates that viral variants were present and/or were generated during the selection process, and were selected based on the property of the occlusion of wild-type levels of viral particles.

TABLE 3

Comparison of virion densities within polyhedra produced in *Lymantria dispar* larvae and in the Ld652Y cell line by in vivolin vitro selected LdMNPV strains.

| | Virion/$\mu m^2$ | | |
|---|---|---|---|
| Viral Isolate | Polyhedra Produced in *L. Dispar* Larvae | Polyhedra Produced in Ld652Y Cells | % Difference Cells vs Larvae |
| A21-12A | 13.1 | 15.9 | +21.4 |
| 2031A1C | 16.6 | 17.7 | +6.6 |
| 2035A1G | 16.2 | 15.2 | −6.2 |
| 2031A1B | 13.9 | 17.5 | +25.9 |

Figure 2:
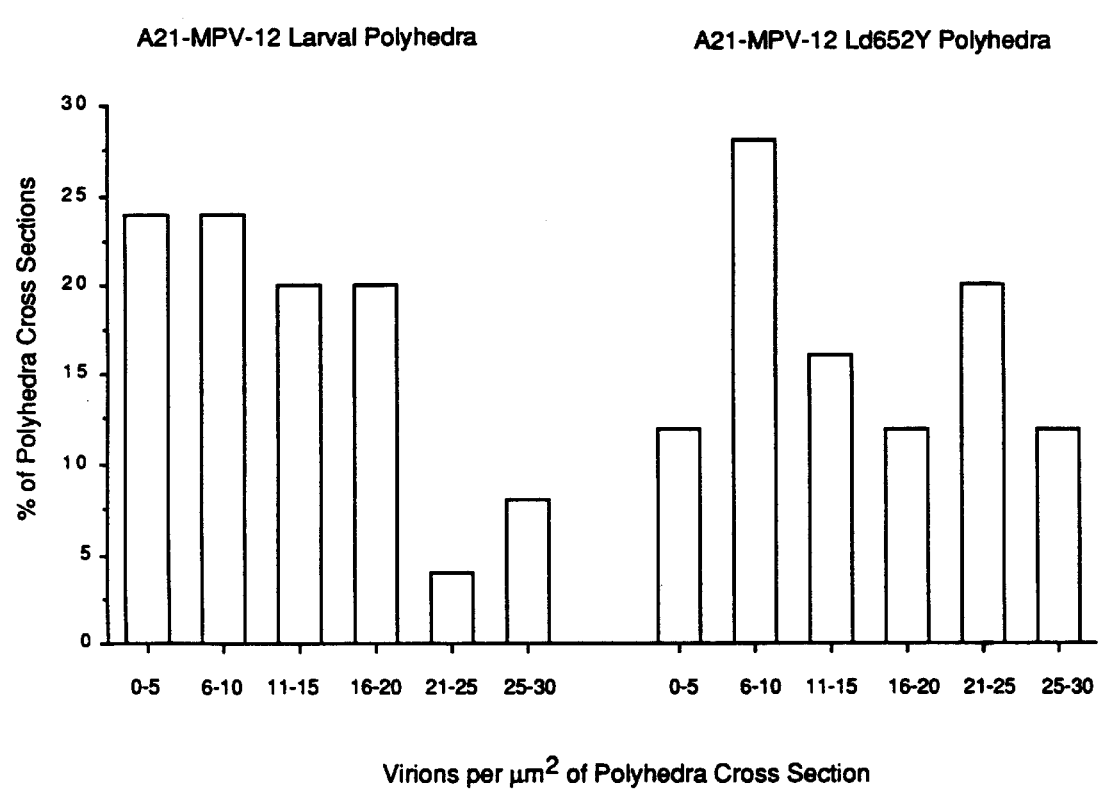

This distribution in ranges of virion densities within polyhedra generated in gypsy moth larvae and the Ld652Y cell line by the selected isolate A21-MPV-12A were compared. The relative virion densities in polyhedra were graphed in the form of the percentage of polyhedra cross-sections containing from 0–5, 6–10, 11–15, 16–20, 21–25, and 25–30 virions per $\mu m^2$ of polyhedra cross-section surface area. The distribution of virion densities in polyhedra produced by isolate A21-MPV-12A in gypsy moth larvae as well as the Ld652Y cell line gave a bell shape curve (FIG. 2). The bell shaped distribution in virion densities within polyhedra generated in the Ld652Y cell line by the selected isolate is in contrast to the distribution in virion densities by wild-type isolates produced in the Ld652Y cell line (FIG. 1).

Polyhedra produced in cell culture and in gypsy moth larvae by the selected viral isolates were then bioassayed to determine potency. The potencies of polyhedra produced in the Ld652Y cell line by the in vivo/in vitro selected viral lines, as determined by bioassay, were found to be slightly less than the potency of polyhedra produced in gypsy moth larvae (Table 4). However, the decreases ranged from approximately 1.5 to 6-fold, which is significantly less than the 20 to 130-fold decrease found with wild-type isolates (Table 1). The basis for the enhanced potency of the in vivo/in vitro selected viral lines produced in the Ld562Y cell line is likely due to the same level of viral nucleocapsid occlusion into polyhedra produced in cell culture compared to polyhedra generated in gypsy moth larvae.

TABLE 4

Comparison of the potencies of selected viral isolates produced in gypsy moth larvae and the Ld652Y cell line.

| Viral Isolate | $LC_{90}$ Larval Polyhedra[a] | $LC_{90}$ Ld652Y Polyhedra[a] | $LC_{90}$ Ld652Y/ $LC_{90}$ Larval |
|---|---|---|---|
| A21-MPV12A | 10,251 | 63,397 | 6.2 |
| 2031A1C | 6586 | 13,021 | 1.5 |

TABLE 4-continued

Comparison of the potencies of selected viral isolates produced in gypsy moth larvae and the Ld652Y cell line.

| Viral Isolate | $LC_{90}$ Larval Polyhedra[a] | $LC_{90}$ Ld652Y Polyhedra[a] | $LC_{90}$ Ld652Y/ $LC_{90}$ Larval |
|---|---|---|---|
| 2035A1G | 5946 | 23,323 | 3.9 |
| 2031A1B | 7842 | 11,563 | 1.5 |

[a]Polyhedra/ml of diet

5. Comparison of the potencies of selected viral strains to the potency of GYPCHEK.

GYPCHEK is the LDMNPV product produced by the Forest Service for use as a gypsy moth control agent. A cell culture produced viral product should be approximately as potent as GYPCHEK in order for the virus product to be competitive in terms of cost. The potency of several selected viral isolates was compared to the potency of GYPCHEK through bioassay as described previously. Three of the selected isolates were as potent or more potent than GYPCHEK (Table 5).

TABLE 5

Comparison of the potency of GYPCHEK produced L. dispar larvae to the potencies of selected LdMNPV isolates produced in the Ld652Y cell line.

| $LC_{90}$ of GYPCHEK Produced in Larvae[a] | Viral Isolate | $LC_{90}$ of Selected Isolates Produced in Ld652Y Cells[a] | Ratio of $LC_{90s}$[b] |
|---|---|---|---|
| 24,797 | A21-MPV-12A | 63,397 | 0.4 |
| 24,797 | 2031A1C | 13,021 | 1.9 |
| 23,602 | 2035A1B | 23,323 | 1.0 |
| 24,797 | 2031A1B | 11,563 | 2.1 |

[a]Polyhedra/ml of diet.
[b]Ratio of the $LC_{90}$ of GYPCHEK/$LC_{90}$ of selected isolates. A ratio greater than 1 indicates that the selected isolate is more potent than GYPCHEK.

6. Viral formulation and application for gypsy moth control.

We envision that a selected isolate, such as 2031AlC, may be applied to insects or insect habitats in a manner similar as that currently used for LDMNPV. The virus must be ingested by the insect to be effective. However, insects may also become infected as a consequence of ingestion of virus present on the insect or on insect egg masses. Therefore, in the case of plants, the virus will typically be applied to leaf surfaces.

LDMNPV has been formulated as described below for gypsy moth control:

10 grams GYPCHEK ($5.0 \times 10^{10}$ polyhedra per gram)

227 grams (6% wt/vol) Orzan LS (a sunscreen, ITT Raynonier, Seattle, Wash.)

0.47 liters (12.5% by vol) Pro Mo liquid supplement (Southern States Cooperative, Richmond, Va.)

77.6 ml (2% by vol) RHOPLEX B60A (a sticker-spreader, Rohm and Haas Company, Philadelphia, Pa.).

3.24 liters (85.5% by vol) water

A similar, or state of the art, preparation is envisioned for the isolate of the present invention.

The amount of virus to be administered to the insect or the insect habitat is an amount effective to reduce insect infestation as predetermined by routine testing. If the ultimate response is insect mortality, an "insecticidally effective amount" is defined to be those quantities of virus which will result in a significant mortality rate of a test group, as compared to an untreated group. The insecticidally effective amount may vary with the species of pest, stage of larval development, the type of vehicle or carrier, the period of treatment and other factors.

It is often advantageous to apply inoculants with a carrier. Suitable agronomically acceptable carriers are known in the art. Inert solids, such as cellulose or sugars, wetable powders, and aqueous surfactant mixtures are illustrative of suitable chemical carriers. Depending on many factors, the concentration of virus in the final composition may vary, but would include an insecticidally effective amount which may typically be between $1 \times 10^8$ to $1 \times 10^{11}$ polyhedra per liter, but the preferred embodiment would be between $1 \times 10^{10}$ to $1 \times 10^{11}$ polyhedra per liter.

Aerial application of GYPCHEK has been as follows: A448 kW (600 hp) Grumman AGCAT airplane equipped with 8 MICRONAIR AU 5000 Atomizers can be used for LdMNPV application. Delivery of formulated virus could be from $1.0 \times 10^{11}$ to $5.0 \times 10^{11}$ polyhedra in 7.5 liters per acre at an airspeed of 160 km/h. (Podegwaite, et al., *J. Economic Entomology* 85:1136–1139).

I claim:

1. A method for isolating a LdMNPV strain that maintains normal levels of virion occlusion when produced in an insect cell line, comprising the steps of:

(a) infecting gypsy moth larvae with a strain of LdMNPV, (b) harvesting the larvae to collect budded virus within the insect hemolymph, (c) infecting an insect cell line and propagating the cell line in a bioreactor with the budded virus preparation, (d) harvesting virus from the insect cell line, (e) repeating the infection cycle of steps (a)–(d) until one has enriched for a LdMNPV strain with normal levels of occlusion, and (f) confirming that the strain has at least normal levels of occlusion.

2. The method of claim 1 wherein the insect cell line is LdG52Y.

3. The method of claim 1 wherein the cycle of steps (a)–(d) is repeated at least three times.

4. The method of claim 1, wherein the resulting virus is additionally assayed for potency.

5. The method of claim 1 wherein the viral infection dose in step (a) is adjusted to a dose that results in a percentage of mortality that ensures that some of the insects are infected with one virus particle.

6. The method of claim 1 wherein the strain has a level of occlusion that is greater than wild-type.

7. The method of claim 1 wherein the strain of step (e) is plaque-purified before step (f).

8. A LdMNPV strain produced by the method of claim 1.

9. The method of claim 4 wherein the potency is at least 90% that of GYPCHEK.

10. A LdMNPV strain produced by the method of claim 4.

11. The method of claim 5 wherein the infection of step (a) results in insect mortality between 5% and 40%.

12. The method of claim 11 wherein the mortality is between 10% and 25%.

* * * * *